United States Patent [19]
Bechard

[11] Patent Number: 5,302,123
[45] Date of Patent: Apr. 12, 1994

[54] DENTAL HANDPIECE LUBRICATION PURGING APPARATUS

[76] Inventor: Craig A. Bechard, 3 Ridgewood Ter., Barre, Vt. 05641

[21] Appl. No.: 410
[22] Filed: Jan. 4, 1993
[51] Int. Cl.⁵ .......................... A61C 1/02; A61C 1/08; A61C 3/02
[52] U.S. Cl. ..................... 433/104; 433/88; 433/77
[58] Field of Search ...................... 433/104, 27, 77, 80, 433/82, 88

[56] References Cited

U.S. PATENT DOCUMENTS

| | | | |
|---|---|---|---|
| 3,106,021 | 10/1963 | Borden | 433/104 |
| 3,963,391 | 6/1976 | Thorburn et al. | 433/104 X |
| 4,544,355 | 10/1985 | Eibofner et al. | 433/104 |
| 4,902,226 | 2/1990 | Elliott et al. | 433/104 |
| 4,990,087 | 2/1991 | De Rocchis et al. | 433/104 |
| 5,054,584 | 10/1991 | Hoffman | 184/55.1 |
| 5,127,830 | 7/1992 | Sheridan et al. | 433/77 |

*Primary Examiner*—Gene Mancene
*Assistant Examiner*—Cindy A. Cherichetti
*Attorney, Agent, or Firm*—Thomas N. Neiman

[57] ABSTRACT

The apparatus is adapted for maintaining air/gas operated dental drills, mechanical scalers or other tools by blowing air/gas through the handpiece to purge it from excess substances in order to enhance the life of the toll and meet the requirements of health and safety regulations. The apparatus has an absorbant filter sleeve that will serve to surround the instruments to be purged and an internal filter. It uses a rigidly anchored coupling that can be replaced, as desired. It also uses pneumatic tubing and shuttle valves to direct the air/gas flow along with switches that control the power and operation of the apparatus. A pressure gauge is mounted on the housing to allow the user to observe the pounds per square inch pressure being used in the purging operation. A timer controlling the amount of time the instruments are being purged is also incorporated. A number of ports are used to allow connection air, water and fiber optic lines to the apparatus and exhaust ports are also available.

1 Claim, 3 Drawing Sheets

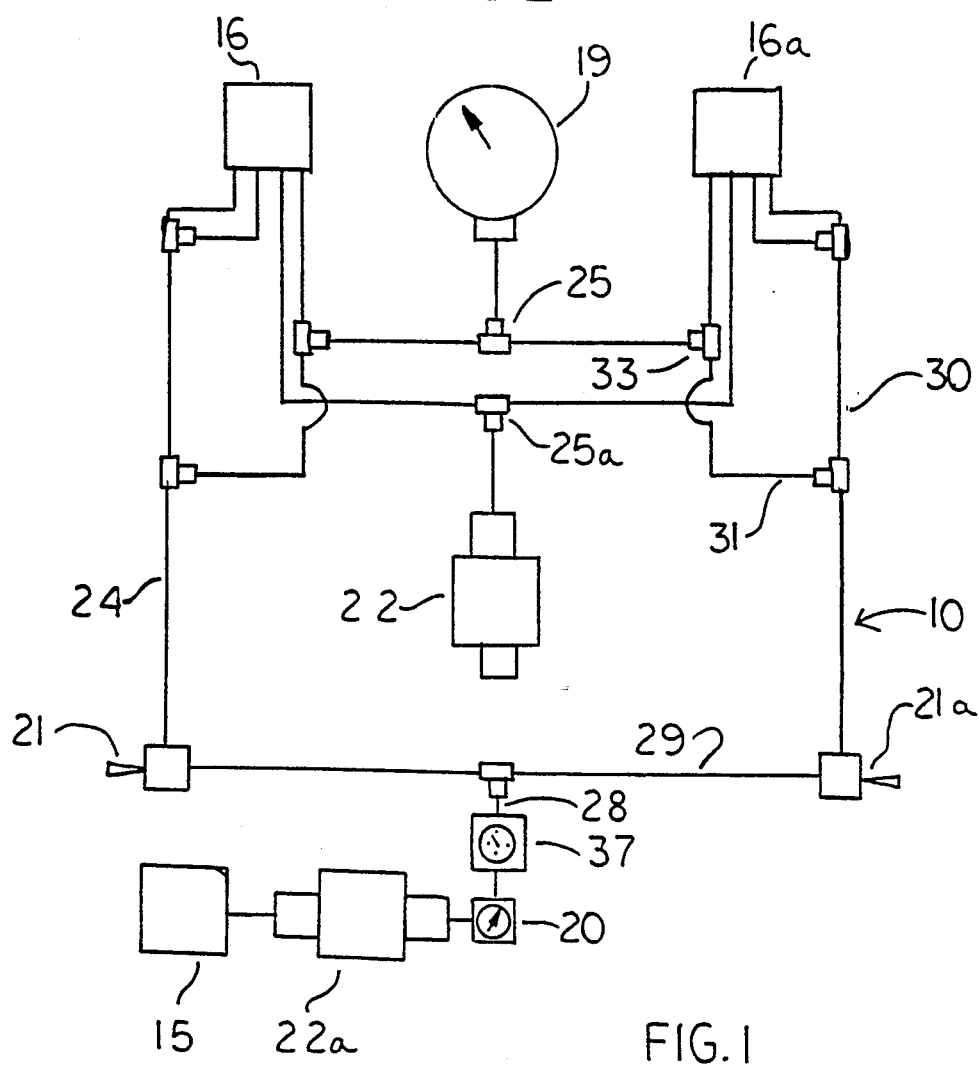
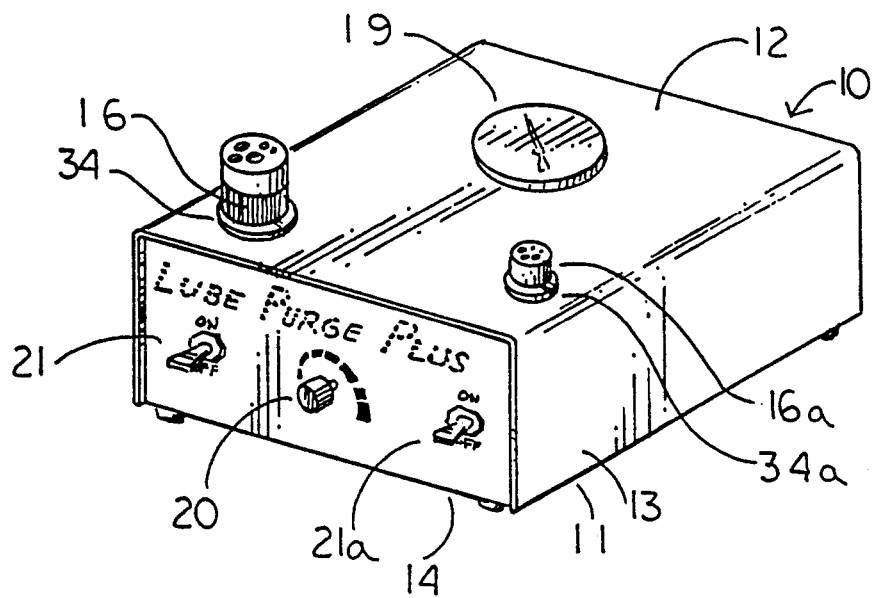

DENTAL HANDPIECE LUBRICATION PURGING APPARATUS

BACKGROUND OF THE INVENTION

This invention pertains to dental tool purging apparatus and, in particular, to a dental handpiece lubrication purging apparatus that is designed to maintain dental handpieces while, at the same time, meeting all health and safety regulations.

There have been a number of new regulations that require proper removal of excess lubricants that are required to maintain air or gas powered high and low speed drills, mechanical scalers, mechanical condensers and other dental tools. There have been a number of attempts to deal with this problem. The United States Patent issued to J. J. Valeska, U.S. Pat. No. 3,556,669 on Jan. 19, 1971 shows a system for fluid control in dental instruments which details an adjustable air pressure controls and valving means for controlling the air pressure to a number of different handpieces. The U.S. Pat. No. 4,902,226 issued to Raymond D. Elliott on Feb. 20, 1990 shows a dental air supply system which consists of a plurality of modular sections that allows the user to accomplish a plurality of dental functions that are necessary.

What is needed is an apparatus which can be connected to any air or gas driven dental tool for the purpose of blowing air and gas through the tool's inlet ports and purging it of any excess substance within those tubes or chambers. The apparatus is designed to entrap those substances as they are blown or purged into an internal filter or an external flexible sleeve, without requiring the instrument being cleaned to be held by an individual.

It is the object of this invention to teach a dental handpiece lubrication purging apparatus which avoids the disadvantages and limitations, recited above. Another object of this invention is to provide an apparatus that is simple to operate, extremely effective and very cost effective with great ease of connection with a number of different style handpieces. It is also the object of this invention to teach an apparatus which has a multiple task capability, timing control and can be easily connected with the existing air supply found in all dental offices.

SUMMARY OF THE INVENTION

Particularly, it is the object of this invention to teach a dental handpiece lubrication purging apparatus, for use in dental offices in order to meet regulations regarding health and safety requirements, comprising a housing; said housing comprising a top surface, a base surface and a perimeter surface; at least one coupling means positioned on the exterior surface of said housing for permitting quick attachment and release of dental handpieces; a tubing network connected to said couplings to allow the passage of air and gas throughout the network; measuring means for determining the pressure of the air and gas positioned on the said external surface; said tubing network having valve means for directing the flow of air and gas; regulation means for controlling the flow of air and gas to said couplings; switch means; means for filtering the excess materials from said dental handpieces positioned within said housing; and cover means to be positioned over said dental handpiece to keep any spray from the atmosphere.

BRIEF DESCRIPTION OF THE DRAWINGS

Further objects and features of this invention will become more apparent by reference to the following description taken in conjunction with the following figures, in which:

FIG. 1 is a perspective view of the novel dental handpiece lubrication purging apparatus;

FIG. 2 is a schematic view thereof;

DETAILED DESCRIPTION OF THE PREFERRED EMBODIMENT

Figure 3:
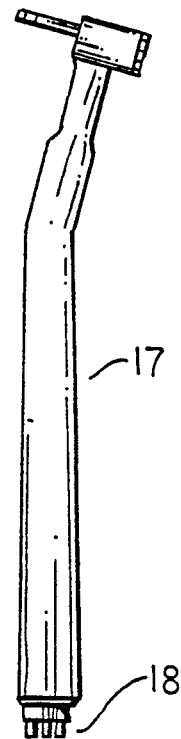
FIG. 3 is a side elevational view of a dental handpiece.
Figure 4:
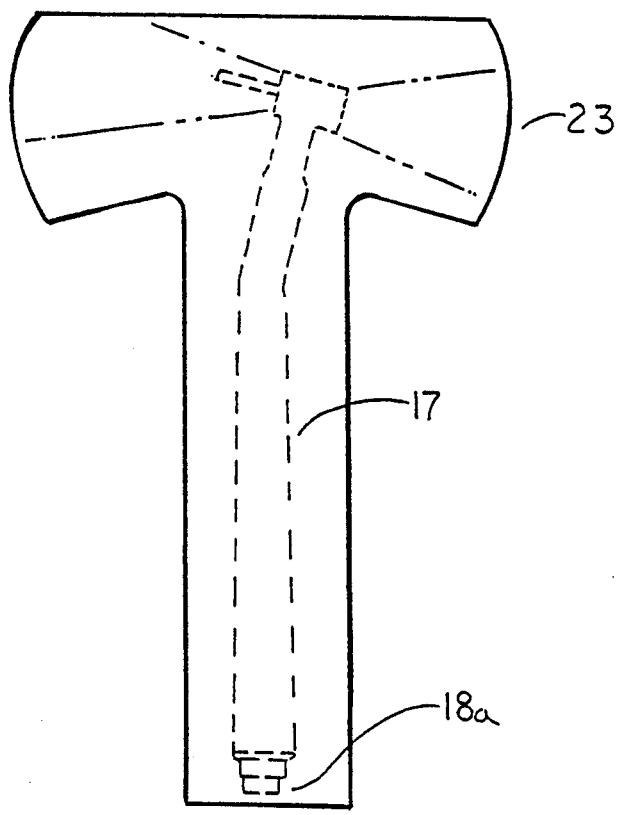
FIG. 4 is a side elevational view of the dental handpiece with the cover installed.
Figure 5:
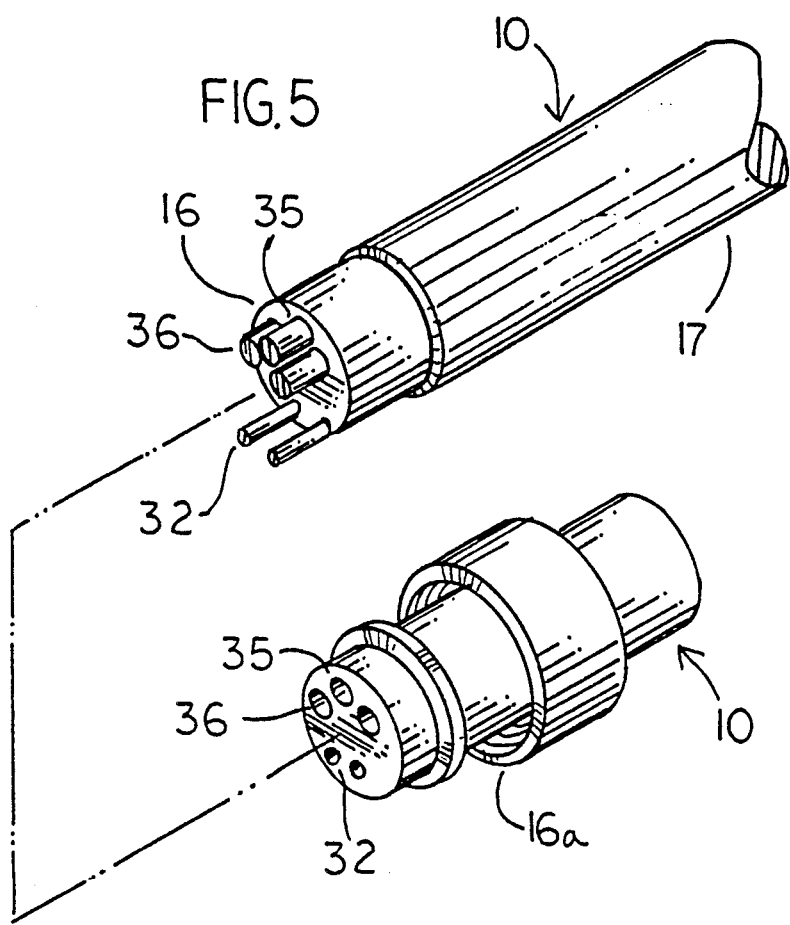
FIG. 5 is a perspective view of a pair of handpiece connection couplings.
Figure 6:
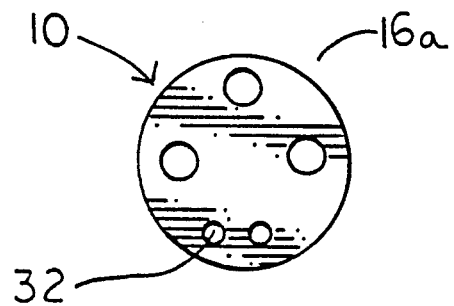
FIG. 6 is a top plan view of the air and fluid ports in a coupling.

As shown in the figures, the novel apparatus 10 comprises a housing 11 with an upper or top surface 12, a perimeter surface 13 and a base surface 14. The apparatus 10 is connected to the dental office's air supply line or a separate air or gas supply by attaching a threaded fitting 15. The apparatus has couplings 16 and 16a to which a handpiece 17 that has one of a number of different fittings 18 and 18a. A timer can be added that controls the length of time for which the air or gas is delivered to the gauge and regulator. The apparatus also has a gauge 19 and a flow regulator 20 that controls the flow volume of the air or gas.

The apparatus has an on/off switch 21 and 21a which cuts off flow to the couplings 16 and 16a. The apparatus has an internal filtration unit 22 which is designed to receive the excess lubricant that is purged from the handpiece 17 and a filtration unit 22a that delivers clean air to the unit. The filtration unit 22 is attached to the base surface 14 by means of a filter clip that allows the filter to be removed as necessary for cleaning. An absorbent filter sleeve or cover 23 is designed to fit over the handpiece 17 in order to receive any spray from the handpiece when it is purged.

The apparatus has an extensive tubing network 24 which allows passage of the air or gas through the threaded fitting 15 through the regulator 20 an into the tubing system 24. After the handpiece is lubricated, while it is in the sleeve 23 it is attached to the appropriate coupling 16 or 16a. When the appropriate switch 21 or 21a or the timer 37 is activated the action of the handpiece is initiated. The user sets the required pressure for the specific handpiece by means of the pressure regulator 20 as read off of the pressure gauge 19. A shuttle valve 25 or 25a prevents air or gas flow from reaching the unused coupling 16 or 16a and allows the pressure gauge to sense the pounds per square inch pressure.

A more detailed description of the air or gas flow patterns using switch 21a and coupling 16a shows the following pattern. As the air flows through the tube 28 and goes into tube 29 through switch 21a and into tube 30. The air then branches off into tubing 31 which blows air through the air port 32 into the coupling 16a and into the handpiece 17. The air also continues up tubing 30 which drives the operation of the handpiece through the drive air port 35 which blows out excess lubrication and fluids from the handpiece 17 into the external filter sleeve 23. Other excess materials are spun by the action of the handpiece 17 through the exhaust port 36 and into tubing 33 into shuttle valve 25a and into the internal filtration unit 22. The filtration unit 22 has a filter exhaust to permit filtered air to escape from the filtration unit 22 through a hole in the rear of the apparatus housing. When the filtration unit is saturated with materials, it is removed from the holding clip and replaced.

As it can be appreciated, there are a number of different types of handpieces with a number of different fittings. Two of the more standard units have been illustrated. But the apparatus has been designed to have the couplings anchored while they are being used and removable by the use of a specially designed threaded ring 34 and 34a around the coupling. The threaded ring releases the coupling and a coupling with a different desired fitting is attached.

While I have described my invention in connection with specific embodiments thereof, it is clearly to be understood that this is done only by way of example and not as a limitation to the scope of my invention as set forth in the objects thereof and in the appended claims.

I claim:

1. A dental handpiece lubrication purging apparatus, for use in dental offices in order to meet regulations regarding health and safety requirements, comprising:

a housing;

said housing comprising a structure having a top surface, a base surface and a perimeter surface;

at least one coupling means positioned on the exterior surface of said housing for permitting quick attachment and release of dental handpieces;

said coupling means having a plurality of port means;

said port means comprising orifice means for the passage of gaseous elements, fluids and fiber optics;

said coupling mean further having threading means for the attachment or removal of many types of handpieces and quick release disconnects;

a tubing network connected to said couplings to allow the passage of air and gas throughout the network;

said tubing network comprising a plurality of flexible tubes that direct the flow of air and gas to said ports as necessary;

measuring means for determining the pressure of the air and gas positioned on said exterior surface;

said measuring means comprising an air and gas pressure gauge;

said tubing network having valve means for directing the flow of the air and gas;

regulation means for controlling the flow of air and gas to said couplings;

said regulation means comprising a regulator that allows the user to accurately control the flow of air and gas;

switch means;

said switch means comprising a two way, on and off, flow system;

said switch means further comprising a timing mechanism for controlling the amount of time that the handpieces are purged;

means for filtering the excess materials from said dental handpieces positioned within said housing;

said filtering means having clip means attached to said base of said housing to retain said filtering means in position within said housing;

said filtering means further having exhaust means for permitting clean purged air to exit from said apparatus;

said housing means further comprising means for supporting said couplings said measuring means and said switch means;

cover means to be positioned over said dental handpiece to keep any spray from the atmosphere; and said cover means comprising an absorbant filter sleeve that allows said dental handpiece to be inserted within said sleeve to minimize blowback when the handpiece is lubricated or purged.

* * * * *